United States Patent
Muzzammel

[11] Patent Number: 6,132,406
[45] Date of Patent: Oct. 17, 2000

[54] HYSTEROSONAGRAM/ HYSTEROSALPINGORAM CANNULA WITH SOFT SEAL

[76] Inventor: Mohiuddin M. Muzzammel, 11323 Bright Pond La., Reston, Va. 20194

[21] Appl. No.: 09/315,152

[22] Filed: May 20, 1999

[51] Int. Cl.$^7$ .................................................. A61M 31/00
[52] U.S. Cl. ........................ 604/279; 604/104; 604/96.01
[58] Field of Search .............................. 604/96, 104, 279, 604/286, 287

[56] References Cited

U.S. PATENT DOCUMENTS

| | | |
|---|---|---|
| 85,995 | 1/1869 | Buffon . |
| 3,385,300 | 5/1968 | Holter . |
| 3,796,211 | 3/1974 | Kohl . |
| 3,971,385 | 7/1976 | Corbett . |
| 4,585,438 | 4/1986 | Makler . |
| 5,195,964 | 3/1993 | Kletzky et al. . |

*Primary Examiner*—Sharon Kennedy
*Assistant Examiner*—Eric Kline
*Attorney, Agent, or Firm*—Patent & Trademark Services; Joseph H. McGlynn

[57] ABSTRACT

A single channel cannula which has a semi-rigid hollow shaft and a soft seal for both a fluid seal and to prevent the cannula from slipping out of position during medical procedures. The cannula may be straight, curved or angled at the distal inner end and may have a flexible segment at the proximal outer end for insertion of a syringe or other fluid source.

8 Claims, 1 Drawing Sheet

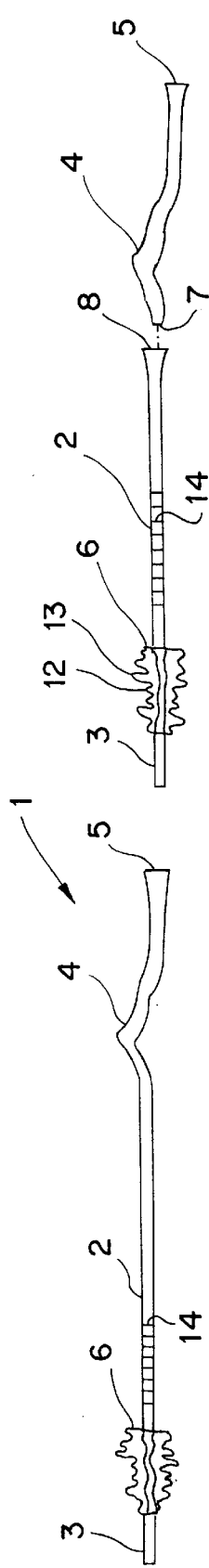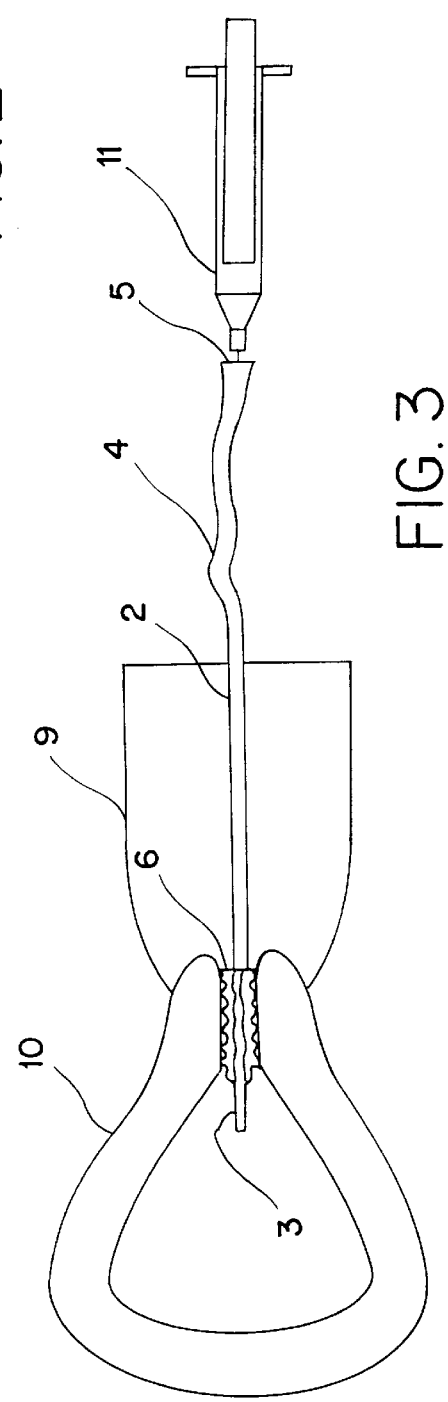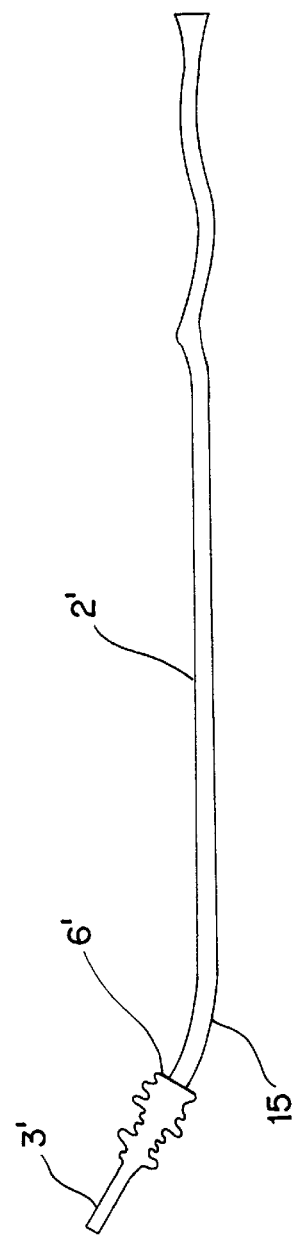

HYSTEROSONAGRAM/ HYSTEROSALPINGORAM CANNULA WITH SOFT SEAL

This application is related to Ser. No. 09/220,066, filed Apr. 2, 1998, pending.

BACKGROUND OF THE INVENTION

This invention relates, in general, to a single channel cannula, and, in particular, to a single channel cannula with a soft seal attached thereto.

DESCRIPTION OF THE PRIOR ART

In the prior art various types of cannula have been proposed. For example, U.S. Pat. No. 85,995 to Buffon discloses a syringe with a soft sponge surrounding a rigid shaft to collect waste fluid.

U.S. Pat. No. 3,385,300 to Holter discloses a cervical cannula having a shaft and a tapered cone shaped seal made from a flexible material.

U.S. Pat. No. 3,796,211 to Kohl discloses a biopsy sampler having a shaft surrounded by a cone shaped seal.

U.S. Pat. No. 4,585,438 to Makler discloses a injector with a semi-rigid tubular member surrounded by a seal.

U.S. Pat. No. 5,195,964 to Kletzky et al discloses a cannula with a flexible shaft and a cone shaped seal which is retained in place by a forceps.

SUMMARY OF THE INVENTION

The present invention is directed to a single channel cannula which has a semi-rigid hollow shaft and a soft seal for endocervix for a fluid seal, and to prevent the cannula from slipping out of position during medical procedures.

It is an object of the present invention to provide a new and improved cannula with a soft seal surrounding one end, which will hold the cannula in position during medical procedures.

It is an object of the present invention to provide a new and improved cannula with a semi-rigid shaft to enhance the maneuverability of the cannula.

It is an object of the present invention to provide a new and improved single channel cannula with a soft seal for endocervix using a sponge or similar material to minimize patient discomfort, and as a fluid seal at the cervical canal during fluid injection into the uterine cavity.

These and other objects and advantages of the present invention will be fully apparent from the following description, when taken in connection with the annexed drawings.

BRIEF DESCRIPTION OF THE DRAWINGS

FIG. 1 is a side view of the present invention.

FIG. 2 is a side view of another embodiment of the present invention.

FIG. 3 is a side view of the present invention with the cannula in use.

FIG. 4 is a side view of another embodiment of the present invention

DESCRIPTION OF THE PREFERRED EMBODIMENT

Referring now to the drawings in greater detail, FIG. 1 shows the cannula 1 of the present invention. The cannula has a first end 5 which is cone-shaped in order to receive instruments such as a syringe 11, as shown in FIG. 3. Adjacent to the first end 5 is a flexible segment 4 which can be used by the physician to manipulate the instrument during the procedure. Connected to the flexible segment 4 is a relatively straight, single channel, hollow segment 2. This segment should be made from a material that is semirigid which will allow the physician to more easily manurer the cannula through the vagina 9 and into the cervix 10, as shown in FIG. 3.

The cannula of the prior art make this segment rather flexible, which can make maneuvering the cannula difficult, and due to the flexibility of the prior art cannula, it can kink or bend during insertion. If the cannula is bent, it will be difficult or impossible to insert instruments or medication through the hollow cannula and have the instruments or medication delivered to the desired location. With the semi-rigid nature of the shaft segment 2 the physician can be assured that the cannula 1 will not kink or bend, thereby blocking the internal passage through the cannula for instruments or medication. Also, the semi-rigid nature of the shaft segment 2 will make it easier for the physician to manurer the cannula as he/she inserts the instrument.

Another problem with the prior art cannula is that the seal or seating member that surrounds the distal end 3 is made from a relatively smooth, hard material. For example, the seal 44, shown in the Kletzky et al reference (U.S. Pat. No. 5,195,964), is made from a semi-rigid silicone rubber or plastic, and, as shown in FIG. 3 a of Kletzky et al, a forceps is used to keep the cannula in place which is painful to the patient. The alternative solution shown in the prior art has been to make the outer surface of the seals with irregularities such as the teeth 16 shown in the Holter reference (U.S. Pat. No. 3,385,300). While the teeth of Holter will secure the seal more firmly in place, they can also cause irritation to the patient.

The cone-shaped seal 6 of the present invention solves these problems by making the seal 6 from a soft material such as the material used to make sponges. The soft material will prevent irritation to the patient as the physician inserts and manurers the cannula. In addition, the introduction of the soft material of the seal 6 into the cervical canal, as shown in FIG. 3, will allow the seal to contact the inner walls of the opening to the cervix 10 and to firmly, but gently, secure the seal in place. In addition, the outer surface of the soft material of the seal 6 has a plurality of irregular valleys 12 and lands 13, as shown in FIGS. 1, 2 and 3, which will allow the seal to contact the inner walls of the opening to the cervix 10 and to firmly, but gently, secure the seal in place. Therefore, when the seal 6 is in position, there will be little, if any irritation to the patient because of the soft material of the seal. In addition, the soft seal being in the cervical canal will assure that the cone-shaped seal is fly secured in place and will not become dislodged as the physician manurers instruments (not shown) through the hollow cannula, or inserts medication through the cannula by means of the syringe 11.

The embodiment shown in FIG. 2 is essentially the same as the FIG. 1 embodiment except the FIG. 2 embodiment is made in two parts with the shaft 2' separate from the flexible segment 4 and the end 5. This will make it easier to make the shaft 2' from a different material than the portion containing the flexible segment 4. That is the shaft 2' can be made from a semi-rigid material and the portion containing the flexible segment 4 can be made from a softer material. Also, the end 8 on the shaft 2' should be made cone-shaped in order to more easily receive the end 7. Indicia markings 14, preferably in centimeters, are marked along the shaft 2, 2' in any conventional manner. In all other respects the embodiment shown in FIG. 2 is essentially the same as the FIG. 1 embodiment and works in the same manner.

The embodiment shown in FIG. 4 is essentially the same as the FIG. 1 embodiment, except the distal end 3', adjacent the soft seal 6' is angled at 15 with respect to the shaft 2'. This angle between the distal end 3' and the shaft 2' will make it easier to insert the cannula into the uterus.

Although the Hysterosonogram/Hysterosalpingogram Single Channel Cannula with Soft Seal and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What is claimed as my invention is:

1. A cervical cannula comprising:

a shaft having a first end and a second end, said first end having means for introducing instruments into an interior of said shaft, said second end of said shaft having a seal surrounding said shaft adjacent said second end, said seal made from a material that is softer than said shaft, said seal having an irregular surface irregularly positioned around a periphery of said seal, said second end being disposed at an angle greater than 90° with respect to a longitudinal axis of said shaft.

2. The cervical cannula as claimed in claim 1, wherein said cervical cannula has a flexible outer segment.

3. The cervical cannula as claimed in claim 2, wherein said cervical cannula has a syringe receiving terminal at the end of the flexible segment.

4. The cervical cannula as claimed in claim 1, wherein said means for introducing instruments into an interior of said shaft is a funnel shaped opening.

5. The cervical cannula as claimed in claim 1, wherein said seal is cone shaped with a smaller end of said seal positioned closer to said second end than a larger end of said seal.

6. The cervical cannula as claimed in claim 1, wherein said seal is made from a sponge material.

7. The cervical cannula as claimed in claim 1, wherein said shaft has indicia markings in centimeters along the shaft.

8. The cervical cannula as claimed in claim 1, wherein said irregular surface is comprised of a plurality of valleys and lands, and wherein some of said valleys are deeper than others of said valleys, and some of said lands are higher than others of said lands.

* * * * *